(12) United States Patent
Shibuya et al.

(10) Patent No.: US 7,163,944 B2
(45) Date of Patent: Jan. 16, 2007

(54) CYCLIC DIAMINE COMPOUND AND PHARMACEUTICAL CONTAINING THE SAME

(75) Inventors: Kimiyuki Shibuya, Tokorozawa (JP); Toru Miura, Higashimurayama (JP)

(73) Assignee: Kowa Co., Ltd., Nagoya (JP)

( * ) Notice: Subject to any disclaimer, the term of this patent is extended or adjusted under 35 U.S.C. 154(b) by 319 days.

(21) Appl. No.: 10/763,241

(22) Filed: Jan. 26, 2004

(65) Prior Publication Data

US 2005/0165026 A1    Jul. 28, 2005

(51) Int. Cl.
*A61K 31/496*    (2006.01)
*C07D 413/12*    (2006.01)
(52) U.S. Cl. .................. 514/254.01; 544/368
(58) Field of Classification Search ............... 544/368; 514/254.01
See application file for complete search history.

(56) References Cited

FOREIGN PATENT DOCUMENTS

WO    WO 98/54153    12/1998
WO    WO 03/018564    3/2003

OTHER PUBLICATIONS

Kawaguchi et al. Chemical Abstracts, vol. 123, No. 222345 (1995) (Abstract for JP 07167862 (Jul. 4, 1995).*

Vippagunta et al Advanced Drug Delivery Reviews, vol. 48, pp. 3-26 (2001).*
P. J. Gillies, et al., Experimental and Molecular Pathology, vol. 44, pp. 329-339, "Regulation of Acyl-CoA: Cholesterol Acyltransferase Activity in Normal and Atherosclerotic Rabbit Aortas: Role of a Cholesterol Substrate Pool", 1996.
L. Li, et al., Biochimica and Biophysica Acta, vol. 1530, pp. 111-122, "Effects of High-Density Lipoprotein2 on Cholesterol Transport and Acyl-Coenzyme A: Cholesterol Acyltransferase Activity in P388D1 Macrophages", 2001.

* cited by examiner

*Primary Examiner*—Emily Bernhardt
(74) *Attorney, Agent, or Firm*—Oblon, Spivak, McClelland, Maier & Neustadt, P.C.

(57) ABSTRACT

The present invention relates to 2-[4-[2-(7-trifluoromethyl-benzoxazol-2-ylthio)ethyl]piperazin-1-yl]-N-[4-hydroxy-2,6-bis(trifluoromethyl)phenyl]acetamide or salt thereof, and an intermediate for the preparation thereof.

The above-described compound has both an inhibitory action on ACAT in the artery wall and remarkably high metabolic resistance in human liver microsomes, and exhibits excellent effects for suppressing lipids depression in aorta in vivo so that it is useful as a highly effective preventive or remedy for hyperlipidemia and arteriosclerosis with less side effects.

14 Claims, 1 Drawing Sheet

CYCLIC DIAMINE COMPOUND AND PHARMACEUTICAL CONTAINING THE SAME

TECHNICAL FIELD

The present invention relates to a cyclic diamine compound having potent ACAT inhibitory activity and high metabolic resistance, and shows excellent suppressive effects on lipid deposition in the artery, and salts thereof, and intermediates for the preparation of these compounds.

BACKGROUND ART

Acyl coenzyme A cholesterol acyltransferase (ACAT) is an enzyme for the synthesis of cholesterol ester from cholesterol and plays an important role in the metabolism of cholesterol and its absorption in digestive organs. Although many of conventional ACAT inhibitors serving as a therapeutic agent for hyperlipidemia or arteriosclerosis have acted on the ACAT in the small intestine or liver to lower plasma cholesterol level, they disadvantageously have side effects such as intestinal bleeding, intestinal disorder, diarrhea and liver disorder.

According to the recent studies, foamed macrophage is observed in a lesion of atherosclerosis. It has been revealed that the formation of macrophage-derived form cells is closely related to the progress of the lesion. Suppression of the formation of macrophage-derived form cells is expected to lead to the involution of an arteriosclerotic lesion itself. At the arteriosclerotic lesion site, the activity of ACAT in the artery wall has been elevated and cholesterol ester has accumulated on the artery wall so that it is presumed that the ACAT activity in the artery wall has a close relation to arteriosclerosis (Exp. Mol. Pathol., 44, 329–339 (1986)). Accordingly, the inhibition of the ACAT activity in the artery wall can suppress conversion from free cholesterol to cholesterol ester by ACAT. On the other hand, free cholesterol in the cells can be eliminated from the cells by high density lipoprotein (HDL) and conveyed to the liver (reverse transfer by HDL). The free cholesterol in the liver can be metabolized so that accumulation of cholesterol ester at the arteriosclerotic lesion site is expected to be suppressed (Biochim. Biophys. Acta. 2001 15, 1530(1): 111–122).

An agent which inhibits ACAT in the artery wall is thus considered to become a direct remedy for arteriosclerosis and there is accordingly a demand for the exploitation of such a medicine.

Under such situations, finding that cyclic diamine compounds represented by the following formula (A):

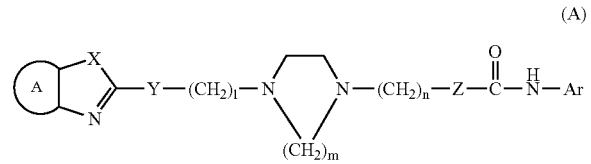

(A)

wherein, Ar represents an aryl group which may be optionally substituted,

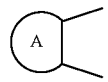

represents a divalent residue of benzene, pyridine, cyclohexane or naphthalene which may be optionally substituted, X represents NH, an oxygen atom or a sulfur atom, Y represents a sulfur atom or the like, Z represents a single bond or the like, l stands for an integer of from 1 to 15, m stands for an integer of 2 or 3 and n stands for an integer of from 1 to 3, or salts thereof, or solvates of these compounds strongly inhibit ACAT in the artery wall and will be a preventive or remedy for arteriosclerosis with less side effects, the present inventors filed a patent application for it (International Publication No. 98/54153). Moreover, the present inventors found that among the compounds represented by the above-described formula (A), the below-described compound (B), salts thereof or solvates thereof have an excellent action as an artery wall-selective ACAT inhibitor and are excellent in oral absorption, and filed a patent application for it (International Publication No. 03/018564).

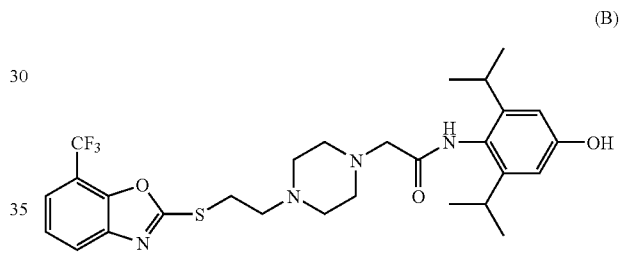

(B)

However, in the in vitro human liver microsome test, Compound (B) was revealed to show low metabolic resistance. Accordingly, there is a demand for ACAT inhibitors capable of strongly inhibiting ACAT in the artery wall as well as having high metabolic resistance.

DISCLOSURE OF THE INVENTION

An object of the present invention is therefore to provide a compound which strongly inhibits ACAT in the artery wall, shows high metabolic resistance in liver microsomes, has less side effects and is clinically useful as a preventive or remedy for arteriosclerosis.

With the foregoing in view, the present inventors have proceeded with further investigations and found that among the above-described cyclic diamine compounds (A), 2-[4-[2-(7-trifluoromethylbenzoxazol-2-ylthio)ethyl]piperazin-1-yl]-N-[4-hydroxy-2,6-bis(trifluoromethyl)phenyl]acetamide (compound (1), the structure thereof shown below) having both a [4-hydroxy-2,6-bis(trifluoromethyl)phenyl]acetamide group and a (7-trifluoromethylbenzoxazol-2-ylthio)ethyl group, or salt thereof is extremely useful as a preventive or remedy for various diseases associated with accumulation of cholesterols, because compound (1) has an inhibitory action on ACAT in the artery wall, has far high metabolic resistance in human liver microsomes compared with Compound (B), and exhibits excellent effects for suppressing lipid deposition in the artery in vivo. The structure of compound (1) is represented by formula (1) shown below.

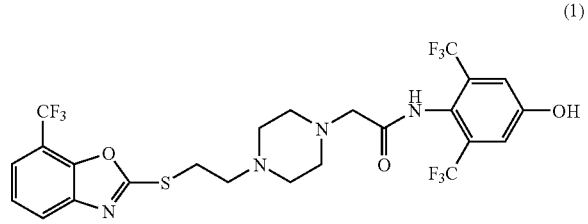

In one aspect of the present invention, there is thus provided 2-[4-[2-(7-trifluoromethylbenzoxazol-2-ylthio)ethyl]piperazin-1-yl]-N-[4-hydroxy-2,6-bis(trifluoromethyl)phenyl]acetamide or salt thereof.

In another aspect of the present invention, there is also provided a pharmaceutical comprising the above-described compound (1) or salt thereof as an effective ingredient.

In a further aspect of the present invention, there is also provided a pharmaceutical composition comprising the above-described compound (1) or salt thereof, and a pharmaceutically acceptable carrier.

In a still further aspect of the present invention, there is also provided a treating method of arteriosclerosis or hyperlipidemia, which comprises administering the above-described compound (1) or salt thereof.

In a still further aspect of the present invention, there is also provided a 2,6-bis(trifluoromethyl)aniline compound or anilide derivative thereof represented by the following formula (2):

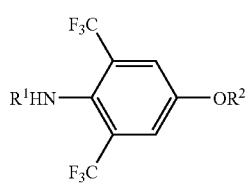

wherein, $R^1$ represents a hydrogen atom or an $XCH_2CO$—group (in which, X is a halogen atom), and $R^2$ represents a protective group selected from lower alkyl groups which may be optionally substituted, lower alkenyl groups which may be optionally substituted, a benzyl group which may be optionally substituted, and a silyl group which may be optionally substituted.

The cyclic diamine compounds of the present invention have both an inhibitory action strongly on ACAT in the artery wall and remarkably high metabolic stability in human liver microsomes, and exhibits excellent effects for suppressing deposition of lipids in the artery in vivo so that they are useful as a highly effective preventive or remedy for hyperlipidemia and arteriosclerosis with less side effects.

BEST MODE FOR CARRYING OUT THE INVENTION

Figure 1:
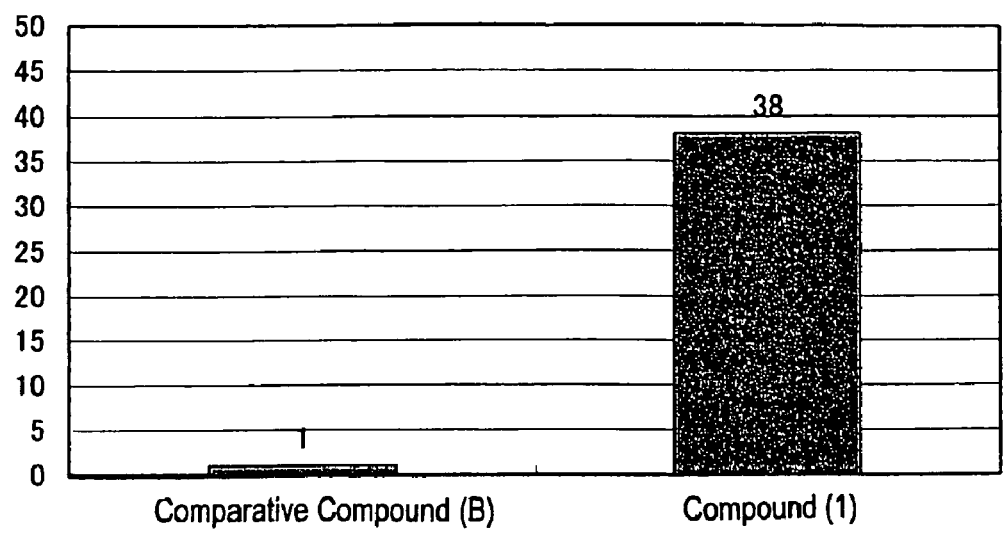
FIG. 1 illustrates the metabolic resistance of a test compound in human liver microsomes.

As is apparent from the below-described formula, the invention compound (1) is a cyclic diamine compound composed of a (benzoxazolethio)ethyl moiety having one trifluoromethyl group on the benzoxazole ring thereof and a (hydroxyphenyl)acetamide moiety having two trifluoromethyl groups on the benzene ring thereof and these two moieties are bound via piperazine. No description on the compound having such a structure is found in the above-described patent documents.

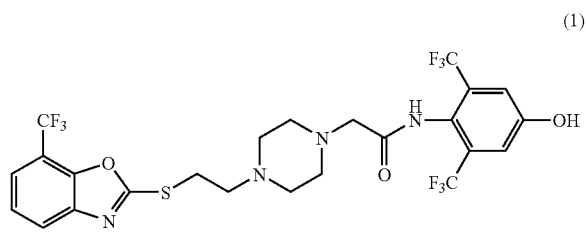

Examples of the salt of the invention compound (1) include inorganic acid salts such as hydrochlorides, sulfates, nitrates and phosphates, and organic acid salts such as methanesulfonates, maleates, fumarates, citrates, butyrates, lactates, tartrates, ascorbates, malates, mandelates, salicylates, pantothenates, tannates, ethanedisulfonates, benzenesulfonates, p-toluenesulfonates, glutamates, aspartates, trifluoroacetates, pamoates and gluconates.

The invention compound (1) or salt thereof may be in the form of a solvate. The compound added with a solvent, for example, water or alcohol, which has been used upon preparation or purification, is a solvate. No particular limitation is imposed on the solvate insofar as it does not adversely affect the ACAT inhibitory action. As the solvate, a hydrate is preferred.

The invention compound (1) is prepared in a desired manner and one example will next be shown.

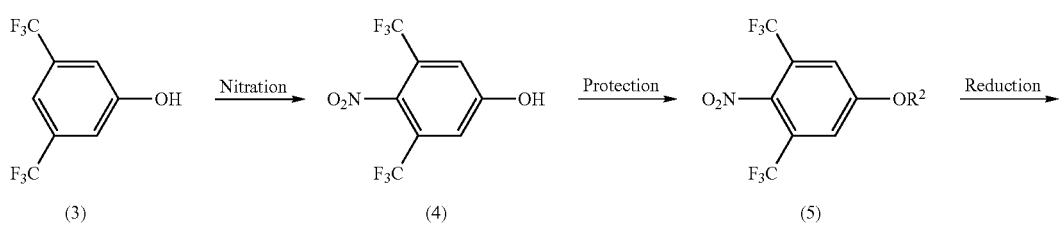

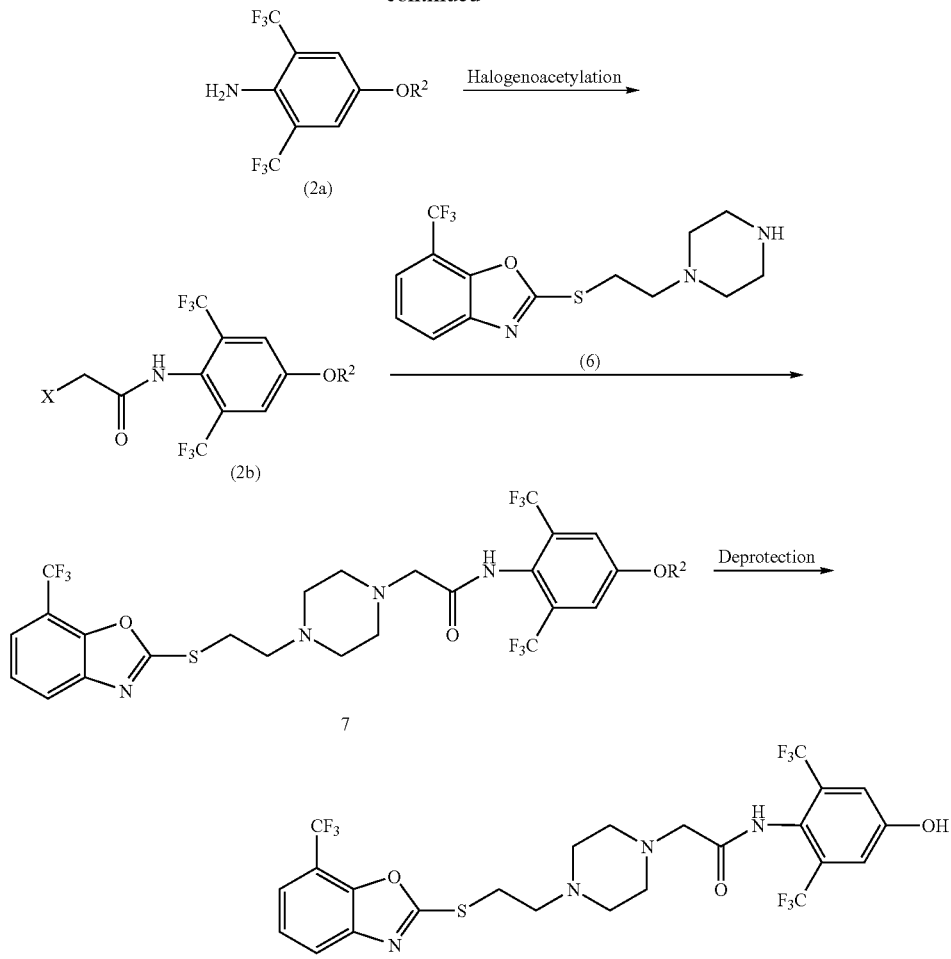

wherein, X represents a halogen atom, R² represents a protective group selected from lower alkyl groups which may be optionally substituted, lower alkenyl groups which may be optionally substituted, a benzyl group which may be optionally substituted, and a silyl group which may be optionally substituted.

Described specifically, the invention compound (1) is available by nitrating 3,5-bis(trifluoromethyl)phenol (3) into 4-nitro-3,5-bis(trifluoromethyl)phenol (4), protecting the hydroxy group of the compound with a protective group represented by R², reducing the nitro group of the resulting compound (5) to obtain compound (2a), reacting it with a halogenoacetic acid or reactive derivative thereof, reacting the resulting halogenoacetamide compound (2b) with 1-[2-[7-trifluoromethylbenzoxazol-2-ylthio]ethyl]piperazine (6) to obtain compound (7), and then eliminating the protective group R² therefrom.

In the above-described reaction scheme, compounds (1), (2a) and (2b) are novel compounds and compounds (2a) and (2b) are useful as intermediates for the preparation of compound (1).

The halogen atoms represented by X include iodine, chlorine and bromine atoms, with a bromine atom being preferred.

As the protective group R² selected from lower alkyl groups which may be optionally substituted, lower alkenyl groups which may be optionally substituted, a benzyl group which may be optionally substituted, and a silyl group which may be optionally substituted, those capable of protecting the hydroxy group from various reactions and being removable easily by hydrolysis, hydrogenolysis or reduction can be used. The term "lower" as used herein means linear or branched $C_{1-6}$ hydrocarbon groups. Specific examples of the lower alkyl groups which may be optionally substituted include methyl, tert-butyl, methoxymethyl, and methoxyethoxy-methyl; those of the lower alkenyl groups which may be optionally substituted include allyl group; those of the benzyl group which may be optionally substituted include benzyl, 4-methoxybenzyl, 2,6-dichlorobenzyl, and 2,6-dimethylbenzyl groups; and those of the silyl group which may be optionally substituted include tert-butyldimethylsilyl, tert-butyldiphenylsilyl and tri-isopropylsilyl groups.

Each step for preparation of the invention compound (1) will next be described.

Nitration of compound (3) may be effected in accordance with Example 1 of Japanese Patent Application Laid-Open No. 167862/1995.

The protective group R² can be introduced into compound (4) based on "PROTECTIVE GROUPS IN ORGANIC SYNTHESIS 3rd Ed." by THEODORA W. GREEN and PETER G. N. WUTS and published by JOHN WILEY & SONS, INC.

Compound (5) is reduced preferably in the presence of 1) a sulfur containing reducing agent such as sodium dithionite, sodium sulfide, sodium bisulfide or hydrogen sulfide, or 2) a metal reducing agent such as zinc, iron or stannous chloride, or 3) catalytically reduced in a hydrogen atmosphere. The reaction using a sulfur-containing reducing agent is carried out, for example, by dissolving compound (5) in a solvent such as isopropanol, ethanol or tetrahydrofuran (THF) and adding to the resulting solution an aqueous solution of the sulfur-containing reducing agent at 80° C. to react them for 10 minutes to 2 hours. The reaction using a metal reducing agent is carried out, for example, by dissolving compound (5) in an alcohol solvent such as ethanol or isopropanol, or acetic acid, or a hydrous solvent thereof and reacting the resulting solution with the metal reducing agent at 0 to 100° C. for 30 minutes to 24 hours. Upon reaction, an acid such as hydrochloric acid or sulfuric acid may be added. The catalytic reduction is carried out by dissolving compound (5) in a single or mixed solvent of dioxane, acetic acid, methanol, ethanol or isopropanol, and reacting at 0 to 50° C. for 30 minutes to 12 hours, preferably at room temperature for 30 minutes to 3 hours in the presence of a catalyst such as Raney-nickel, palladium carbon, palladium hydroxide or palladium black in a hydrogen atmosphere.

Examples of the halogenoacetic acid to be reacted with compound (2a) include chloroacetic acid, bromoacetic acid and iodoacetic acid, while those of the reactive derivative of the halogenoacetic acid include halogenoacetic halides and halogenoacetic anhydrides. Compound (2a) is preferably reacted with the halogenoacetic halide. This reaction between compound (2a) and the halogenoacetic halide is effected, for example, at 0 to 120° C. for 10 minutes to 5 hours in the presence of a base such as N,N-dimethylaniline, triethylamine, pyridine, 4-dimethylaminopyridine or 4-pyrrolidinopyridine in a solvent such as methylene chloride, chloroform, ethyl acetate, acetonitrile or toluene, preferably at 100° C. for 3 to 5 hours in the presence of N,N-dimethylaniline in toluene.

Compound (2b) thus obtained is reacted with compound (6) at room temperature to 50° C. for 5 to 30 hours, preferably at room temperature for 10 to 20 hours in the presence of a base such as potassium carbonate, sodium carbonate, potassium bicarbonate, or sodium bicarbonate in a single or hydrous solvent of N,N-dimethylformamide (DMF), THF or acetonitrile.

The protective group may be eliminated from compound (7) in a known manner, for example, hydrolysis, hydrogenolysis or reduction.

Compound (6) is available by the preparation process described in Example 8 of International Publication No. 03/018564.

As described by Example 8 of Ser. No. 03/018,564, Compound (6) may be produced as described below:

Production of 1-[2-(7-trifluoromethylbenzoxazol-2-yl-thio)ethyl]piperazine ditrifluoroacetate tert-Butyl 4-[2-(7-trifluoromethylbenzoxazol-2-yl-thio)ethyl]-1-piperazinecarb oxylate (37.92 g, 87.9 mmol) was dissolved in trifluoroacetic acid (200 mL) under ice-cooling and stirred at the same temperature for 15 minutes. Ether was added to the reaction solution under ice-cooling and the separated crystals were filtered, washed with ether and dried under a reduced pressure to obtain 47.46 g (yield: 97%) of the target compound as light yellow powdery crystals.

Melting point: 155–156° C. IR (KBr) cm$^{-1}$: 3026, 2421, 1683, 1511, 1596 $^1$H-NMR (d$_6$-DMSO)δ: 2.7–2.90 (4H,m), 2.91–3.04 (2H,m), 3.05–3.22 (4H,m), 3.56 (2H, t, J=6.8Hz), 7.54 (1H, t, J=8. OHz), 7.67 (1H, d, J=8. OHz), 7.96 (1H, d, J=8. OHz), 8.70 (1H, br s). Elementary analysis as C$_{18}$H$_{18}$F$_9$N$_3$O$_5$S Calculated: C, 38.65; H, 3.24; N, 7.51. Found: C, 38.60; H, 3.25; N, 7.51.

The invention compound (1) thus obtained can be isolated or purified by any combination of washing, extraction, recrystallization and various chromatographies. Conversion into the acid addition salt may also be effected in a conventional manner.

Compound (1) obtained in the above-described manner and salts thereof have strong ACAT inhibitory activity at least equal to that of the above-described compound (B) (Test 1) and at the same time, as can be understood from the result of an in vitro test on the metabolic resistance in human liver microsomes (Test 2), are about 40 times higher in metabolic resistance than compound (B). More specifically, in the test, the remaining ratio of the unchanged compound (1) after 30 minutes is 38%, while that of compound (B) is 1%. In the suppression test of the lipid deposition using animal models of arteriosclerosis, the lipid deposition suppression ratio of the compound (1)-administered group is 43%, while that of the compound (B)-administered group is 28%. Thus, compound (1) exhibits marked effects for suppressing deposition of lipids in the artery in vivo (Test 3). Accordingly, the invention compound (1) will be a pharmaceutical useful for various diseases associated with accumulation of cholesterol in the artery wall. Examples of the diseases include hyperlipidemia, arteriosclerosis, cervical and cerebral arteriosclerosis, cerebrovascular disorder, ischemic cardiopathy, ischemic enteropathy, coronary arteriosclerosis, nephrosclerosis, arteriosclerotic nephrosclerosis, arteriolosclerotic nephrosclerosis, malignant nephrosclerosis, acute mesenteric vascular occlusion, chronic mesenteric angina, ischemic colitis, aortic aneurysm and arteriosclerosis obliterans (ASO).

When the invention compound (1) is used as a pharmaceutical or a pharmaceutical composition, the invention compound (1) or salt thereof can be made into a dosage form such as tablets, capsules, granules, powder, injection and suppositories either as it is or together with a pharmaceutically acceptable carrier such as excipient, binder or diluent. Those preparations can be manufactured in a known manner. For example, an oral administrable preparation can be manufactured by formulating the invention compound (1) in desired combination with an excipient such as starch, mannitol and lactose; a binder such as sodium carboxymethyl cellulose and hydroxypropyl cellulose; a disintegrating agent such as crystalline cellulose and calcium carboxymethyl cellulose; a lubricant such as talc and magnesium stearate; a fluidity improving agent such as light silicic anhydride; and so on The pharmaceutical of the present invention can be administered either orally or parenterally, but the former one is preferred.

Dose of the pharmaceutical of the present invention varies depending on body weight, age, sex, symptoms or the like of patients and in the case of adults, administration of 1 to 500 mg/day, preferably 5 to 200 mg/day in terms of the invention compound (1) in one to three portions is preferred.

EXAMPLES

The present invention will hereinafter be described in further detail by Examples. It should however be borne in mind that the technical scope of the present invention is not limited to or by them.

Preparation Example 1

Synthesis of 4-nitro-3,5-bis(trifluoromethyl)phenol

Fuming nitric acid (8.22 mL, 198.2 mmol) was added dropwise to a solution of 3,5-bis(trifluoromethyl)phenol (28.5 g, 123.9 mmol) in acetic acid (300 mL) at about 10° C. After being elevated to room temperature, the mixture was stirred for 43 hours. The reaction mixture was poured into ice water and the resulting solution was extracted with ethyl acetate. The organic layers were combined, washed successively with water and saturated saline, dried over anhydrous sodium sulfate, and distilled under reduced pressure to remove the solvent. The residue was purified by chromatography on a silica gel column (developing solvent; hexane:acetone=15:1→10:1) to yield a crude product. The crude product thus obtained was subjected to sublimation separation under reduced pressure (3 mmHg) at 80° C. by using an evaporator to distill off the isomer, that is, 2-nitro-3,5-bis(trifluoromethyl)phenol, whereby 10.1 g (yield: 29.7%) of 4-nitro-3,5-bis(trifluoromethyl)phenol was obtained as yellow needle-like crystals.

Melting point: 156 to 158° C. IR (KBr): 3412, 3111, 3071, 1611, 1549, 1464. $^1$H-NMR (CDCl$_3$) δ: 6.36 (1H,s), 7.39 (2H,s). EIMS m/z (relative intensity): 275 (M$^+$), 245 (100).

Example 1

Synthesis of 4-benzyloxy-2,6-bis(trifluoromethyl)nitrobenzene

Under ice cooling, potassium carbonate (7.23 g, 52.3 mmol) and benzyl bromide (5.45 mL, 45.8 mmol) were added to a solution of 4-nitro-3,5-bis(trifluoromethyl)phenol (12.0 g, 43.6 mmol) in acetone (250 mL). After stirring at 50° C. for 13 hours, the reaction mixture was filtered and the insoluble matter was washed with acetone. To the residue obtained by distilling the filtrate under reduced pressure, ethyl acetate and water were added to allow it to separate into layers. The aqueous layer was extracted twice with ethyl acetate. The organic layers were combined, washed successively with water and saturated saline, dried over anhydrous sodium sulfate, and distilled under reduced pressure to remove the solvent. The residue was recrystallized from hexane-acetone, whereby 15.0 g (yield: 94.3%) of 4-benzyloxy-2,6-bis(trifluoromethyl)nitrobenzene was obtained as pale yellow needle-like crystals.

Melting point: 141 to 143° C. IR (KBr): 3433, 3118, 3033, 2916, 1617, 1605, 1546. $^1$H-NMR (CDCl$_3$) δ: 5.20 (2H,s), 7.37–7.45 (5H,m), 7.47 (2H,s). EIMS m/z (relative intensity): 365 (M$^+$), 91 (100).

Example 2

Synthesis of 4-benzyloxy-2,6-bis(trifluoromethyl)aniline

Isopropanol (450 mL) was added to 4-benzyloxy-2,6-bis(trifluoromethyl)nitrobenzene (9.00 g, 24.6 mmol) and the latter was dissolved in the former by heating at 70° C. A solution of sodium dithionite (14.1 g, 81.2 mmol) in water (150 mL) was added dropwise to the resulting solution. After stirring for 30 minutes at the same temperature, a solution of sodium dithionite (7.28 g, 41.8 mmol) in water (150 mL) was added further. The reaction mixture was stirred at the same temperature for 14 hours and then, the isopropanol was distilled off under reduced pressure. Ethyl acetate was added to the resulting suspension to separate it into layers. The aqueous layer was extracted with ethyl acetate twice. The organic layers were combined, washed successively with water and saturated saline, dried over anhydrous sodium sulfate, and distilled under reduced pressure to remove the solvent, whereby 8.26 g (yield: 100%) of 4-benzyloxy-2,6-bis(trifluoromethyl)aniline was obtained as colorless needle-like crystals.

Melting point: 58 to 59° C. IR (KBr): 3500, 3425, 3041, 2903, 1645, 1595, 1494. $^1$H-NMR (CDCl$_3$) δ: 4.38 (2H,br s), 5.02 (2H, s), 7.28 (2H,s), 7.31–7.43 (5H,m). EIMS m/z (relative intensity): 335 (M$^+$), 91 (100).

Example 3

Synthesis of N-[4-benzyloxy-2,6-bis(trifluoromethyl)phenyl]-2-bromoacetamide Under an argon atmosphere, N,N-dimethylaniline (2.78 mL, 21.9 mmol) and bromoacetyl bromide (1.91 mL, 21.9 mmol) were added dropwise to a solution of 4-benzyloxy-2,6-bis(trifluoromethyl)aniline (4.90 g, 14.6 mmol) in anhydrous toluene (150 mL) under ice cooling. Immediately after the dropwise addition, the mixture was heated under reflux and then stirred for 1 hour. After cooling, the reaction mixture was filtered through Celite and the insoluble matter was washed with toluene. The residue obtained by distilling the filtrate under reduced pressure was purified by chromatography on a silica gel column (developing solvent; hexane:acetone=10:1→6:1→5:1). The crude product thus obtained was recrystallized from hexane-acetone, whereby 4.31 g (yield: 64.7%) of N-[4-benzyloxy-2,6-bis(trifluoromethyl)phenyl]-2-bromoacetamide was obtained as colorless needle-like crystals.

Melting point: 173 to 175° C. IR (KBr): 3246, 3028, 2997, 1682, 1622, 1516, 1483. $^1$H-NMR (DMSO-d$_6$) δ: 4.01 (2H,s), 5.32 (2H,s), 7.31–7.51 (5H,m), 7.67 (2H,s), 10.2 (1H,s). EIMS m/z (relative intensity): 457 (M$^+$+1), 455 (M$^+$−1), 91 (100).

Example 4

Synthesis of 2-[4-[2-(7-trifluoromethylbenzoxazol-2-ylthio)ethyl]piperazin-1-yl]-N-[4-benzyloxy-2,6-bis(trifluoromethyl)phenyl]acetamide Under ice cooling, a solution of N-[4-benzyloxy-2,6-bis(trifluoromethyl)phenyl]-2-bromoacetamide (4.45 g, 9.75 mmol) in acetonitrile (100 mL) was added dropwise to a solution of 4-[2-[7-trifluorobenzoxazol-2-ylthio]ethyl]piperazine-di-trifluoroacetate (Example 8 of International Publication No. 2003/018564) (5.73 g, 10.24 mmol) and potassium carbonate (6.06 g, 43.9 mmol) in acetonitrile (400 mL). After heating to 50° C., the mixture was stirred for 13 hours. The solvent was then distilled off under reduced pressure. Water and ethyl acetate were added to the residue to separate it into layers. The aqueous layer was extracted with ethyl acetate further. The organic layers were combined, washed successively with water and saturated saline, dried over anhydrous sodium sulfate and distilled under reduced pressure to remove the solvent. The residue thus obtained was purified by chromatography on a silica gel column (developing solvent; chloroform:ammonia-saturated methanol=200:1) to yield 8.50 g (yield: 91.1%) of 2-[4-[2-(7-trifluoromethylbenzoxazol-2-ylthio)ethyl]piperazin-1-yl]-N-[4-benzyloxy-2,6-bis(trifluoromethyl)phenyl]acetamide. The resulting crystals were recrystallized from acetone into colorless needle-like crystals.

Melting point: 156 to 158° C. IR (KBr): 3313, 2947, 2828, 1719, 1702, 1625, 1599. $^1$H-NMR (CDCl$_3$) δ: 2.56–2.80 (8H,m), 2.85 (2H,t, J=6.9 Hz), 3.15 (2H,s), 3.50 (2H,t, J=6.9 Hz), 5.13 (2H,s), 7.34–7.50 (9H,m), 7.76 (1H, d,J=7.8 Hz), 8.82 (1H,s). EIMS m/z (relative intensity): 706 (M$^+$), 91 (100).

Example 5

Synthesis of 2-[4-[2-(7-trifluoromethylbenzoxazol-2-ylthio)ethyl]piperazin-1-yl]-N-[4-hydroxy-2,6-bis(trifluoromethyl)phenyl]acetamide A solution of 2-[4-[2-[7-trifluorobenzoxazol-2-ylthio]ethyl]piperazin-1-yl]-N-[4-benzyloxy-2,6-bis(trifluoromethyl)phenyl]acetamide (6.5 g, 9.2 mmol) and thioanisole (54 mL, 460 mml) in trifluoroacetic acid (100 mL) was stirred at room temperature for 22 hours. After distilling off the solvent under reduced pressure, water and chloroform were added to the residue to separate it into layers. The aqueous layer was extracted with chloroform further. The organic layers were combined, washed successively with water and saturated saline, dried over anhydrous sodium sulfate and distilled under reduced pressure to remove the solvent. The residue thus obtained was purified by chromatography on a silica gel column (developing solvent; hexane:acetone=5:1) to yield 4.91 g (yield: 86.6%) of 2-[4-[2-(7-trifluoromethylbenzoxazol-2-ylthio)ethyl]piperazin-1-yl]-N-[4-hydroxy-2,6-bis(trifluoromethyl)phenyl]acetamide. The resulting crystals were recrystallized from acetone into colorless fine needle-like crystals.

Melting point: 176 to 177° C. IR (KBr): 3203, 2947, 2827, 1679, 1621, 1601, 1507. $^1$H-NMR (CDCl$_3$) δ: 2.55–2.80 (8H,m), 2.85 (2H,t,J=6.9 Hz), 3.21 (2H,s), 3.50 (2H,t,J=6.9 Hz), 6.99 (2H,s), 7.37 (1H,t,J=7.9 Hz), 7.47 (1H,d,J=7.9 Hz), 7.76 (1H,d,J=7.9 Hz), 8.89 (1H,s), 9.09 (1H,s). EIMS m/z (relative intensity): 616 (M$^+$), 98 (100). Elementary analysis: as $C_{24}H_{21}F_9N_4O_3S_1$, Calculated: C, 46.76; H, 3.43; N, 9.09; F, 27.73. Found: C, 46.66; H, 3.51; N, 9.07; F, 27.85

Tests

Test results on the cholesterol ester accumulation inhibitory action, metabolic stability in human liver microsomes and aorta lipid deposition suppressive action of the invention compound (1) will be described in Tests 1 to 3, respectively. As a comparative product, 2-[4-[2-(7-trifluoromethylbenzoxazol-2-ylthio)ethyl]piperazin-1-yl]-N-(2,6-diisopropylphenyl)acetamide (Compound (B)) as described in International Publication No. 03/018564 was employed.

Test 1: Cholesterol Ester Accumulation Inhibitory Action (ACAT Inhibitory Activity) in J774 Cells.

J774 cells (2×10$^5$ cells/well) were seeded on a 24-well plate and incubated for 24 hours in 500 µL of DMEM (10% FBS). After replacement with a new medium, 25-hydroxycholesterol (10 µg/ml) and a test compound (final concentration: 0, 10$^{-9}$ to 10$^{-5}$ mol/L) were added, followed by incubation for 18 hours. After washing with 0.9% NaCl, the lipid was extracted with 250 µL of hexane-isopropanol (3:2) and then extracted with 250 µL of hexane-isopropanol (3:2) again. After the extracts were combined and distilled, the amount of cholesterol ester (CE) thus obtained was determined by the fluorescent enzyme assay. The cells from which the lipid was extracted were subjected to protein assay (micro BCA assay) and the amount of CE per mg of protein was determined. From a CE production ratio of the test compound to the control, IC$_{50}$ (concentration of the compound inhibiting 50% of CE production) was calculated at N=4. The results are shown in Table 1.

It has been confirmed that the invention compound (1) had ACAT inhibitory activity almost as strong as that of Comparative compound (B) shown in Table 1.

TABLE 1

| Test compound | J774:IC$_{50}$ (nM) |
|---|---|
| Invention compound (1) | 49 |
| Comparative compound (B) | 65 |

Test 2: Test on Metabolic Stability in Human Liver Microsomes

In accordance with the below-described Table 2, an NRS (NADPH regenerating system) solution and 16% human serum albumin were added to a 0.1 mol/L phosphate buffer (containing 3.3 mM magnesium chloride) (pH 7.4), followed by the addition of a solution of a test compound (100 µM) in acetonitrile (0.01 mL). After preincubation in a warm bath of 37° C. for 5 minutes, human liver microsomes (POOLED HUMAN LIVER MICROSOMES, Lot. No. 20, product of GENETEST) were added and a reaction was effected for 30 minutes in a warm bath of 37° C. A 0.25 mL portion of the reaction mixture was collected 0 and 30 minutes after the initiation of the reaction, followed by extraction. The amount of the test compound was measured by HPLC. A remaining ratio of the unchanged compound after 30 minutes was calculated based on the following equation: (peak area after 30 minutes/peak area at 0 minute)×100.

As a result, it has been confirmed that the invention compound (1) has drastically improved metabolic resistance (about 40 times higher) in human liver microsomes compared with the comparative compound (B).

TABLE 2

| Composition of the reaction mixture of human liver microsomes (1 mL) | |
|---|---|
| Human liver microsomes (POOLED): containing 1 mg of protein in 0.05 mL | 0.05 mL |
| NRS (NADPH regenerating system) solution: containing, in 0.25 mL of it, 2 mg of β-nicotinamide-adenine dinucleotide, oxidized form type, 2 mg of D-glucose 6-phosphate disodium salt, and 0.8 unit of glucose 6-phosphate dehydrogenase | 0.25 mL |
| 16% human serum albumin | 0.25 mL |
| 0.1 mol/L phosphate buffer (containing 3.3 mM magnesium chloride, pH 7.4) | 0.44 mL |
| An acetonitrile solution of test compound (100 µM) | 0.01 mL |
| Total | 1 mL |

Extraction:

To each sample were added 1.0 mL of a glycine buffer (pH 10), 0.1 mL of an internal standard substance and 5.0 mL of tert-butyl methyl ether, followed by shaking for 10 minutes and centrifugal separation at 2500 rpm for 10 minutes to collect the organic layer.

Test 3: Aorta Lipid Deposition Suppression Test

In accordance with the method of Nicolosi, et al., a test using an animal model of arteriosclerosis, that is, a lipid-loaded F$_1$B hamster model was made and a lipid deposition area in the aortic arch was measured to investigate the effects of the test compound for suppressing lipid deposition [refer to Nicolosi R J, et al., Atherosclerosis 137, 77–85(1988)].

Testing Method:

Bio F₁B male hamsters purchased from Charles River Japan, Inc. were divided at random into three groups (a compound (1) administered group, a comparative compound (B) administered group and a medicament non-administered group (control group)), each group consisting of 6 hamsters. From eight weeks old, they were fed with a fat-rich diet (0.3% cholesterol, 10% coconut oil) for 10 weeks, while a medicament compound was orally administered at a dose of 1 mg/kg twice a day. After 10 weeks, an area of the lipid deposited in the aorta was measured by an image analyser.

Preparation of the Medicament and Administration Method:

The fat-rich diet (0.3% cholesterol, 10% coconut oil) was prepared at a cholesterol:coconut oil:feed (CE-2) mixing ratio of 0.03:1:9. The medicament was orally administered after suspended in a 0.5% methyl cellulose solution. The administered amount of the suspension was 5 mL/kg. Observation of the lipid deposition area in the aorta and its inspection method An 18-G injection needle was inserted into the cardiac apex, followed by perfusion with physiological saline (120 mmHg) for about 5 minutes, and then, with a 4% paraformaldehyde solution (120 mmHg) for about 5 minutes. The heart and thoracic aorta were excised and fixed in a 10% formalin buffer. After fixation, the lesser curvature of the aorta and a portion of the greater curvature were incised and stained with Oil red O. They were opened and attached onto a rubber plate and captured by a digital camera ("Camedia 10", trade name; product of Olympus). The image was scanned into a computer and the area of the portion stained with Oil red 0 and the area of the lumen surface were measured using an image analyser software ("Win Roof", product of Mitani Shoji). In each case of each group, a ratio of the area of the portion stained with Oil Red O to the lumen surface area was calculated and it was designated as an aorta lipid deposition ratio. The aorta lipid deposition suppressing ratio was found from a ratio of the aorta lipid deposition ratio of the medicament administered group to that of the control group. The index was calculated based on the following equation:

Aorta lipid deposition ratio (%)=(area of a portion stained with Oil red O)/(lumen surface area)×100

Aorta lipid deposition inhibiting ratio (%)=1−[(aorta lipid deposition ratio of each group)/(aorta lipid deposition ratio of control group)×100]

Figure 2:
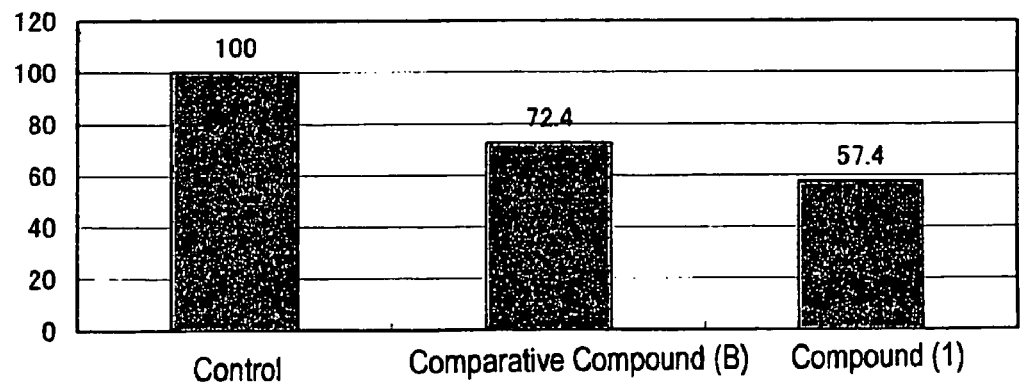
FIG. 2 illustrates the lipid deposition suppressive action of a test compound in the animal model of arteriosclerosis.

The results are shown in FIG. 2. From the diagram, it has been confirmed that the invention compound (1) becomes much superior in a lipid deposition suppressing ratio in the aorta to the comparative compound (B).

Judging from the above-described test results, it has been understood that the invention compound (1) is a very useful substance as an effective ingredient of pharmaceuticals, because it is capable of maintaining a strong ACAT inhibitory action compared with the comparative compound (B), has markedly improved metabolic resistance in liver microsomes, and has thereby marked effects for improving the suppression of lipid deposition in the aorta in the animal test.

This invention claimed is:

1. 2-[4-[2-(7-Trifluoromethylbenzoxazol-2-ylthio)ethyl]piperazin-1-yl]-N-[4-hydroxy-2,6-bis(trifluoromethyl)phenyl]acetamide, or a salt thereof.

2. A pharmaceutical composition comprising 2-[4-[2-(7-trifluoromethylbenzoxazol-2-ylthio)ethyl]piperazin-1-yl]-N-[4-hydroxy-2,6-bis(trifluoromethyl)phenyl]acetamide, or a salt thereof.

3. A method for treating arteriosclerosis or hyper-lipidemia, which comprises:
administering to a subject in need thereof an effective amount of 2-[4-[2-(7-trifluoromethylbenzoxazol-2-ylthio)ethyl]piperazin-1-yl]-N-[4-hydroxy-2,6-bis(trifluoromethyl)phenyl]acetamide or a salt thereof.

4. A compound represented by formula (2):

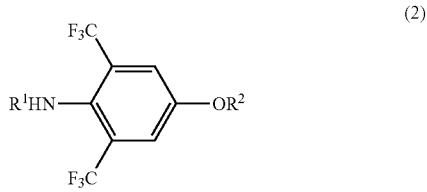

wherein,
R¹ represents a hydrogen atom or an XCH₂CO— group (in which, X is a halogen atom), and R² represents a protective group selected from lower alkyl groups which may be optionally substituted, lower alkenyl groups which may be optionally substituted, a benzyl group which may be optionally substituted, and a silyl group which may be optionally substituted;
with the proviso that when R¹ represents a hydrogen atom, then R² is not substituted C₂–C₄ alkyl;
or a salt of said compound.

5. The compound of claim 4, where R¹ represents a hydrogen atom.

6. The compound of claim 4, where R¹ represents XCH₂CO—, in which, X is a halogen atom.

7. The compound of claim 4, where R² represents a lower alkyl group which may be optionally substituted.

8. The compound of claim 4, where R² represents a lower alkenyl group which may be optionally substituted.

9. The compound of claim 4, where R² represents a benzyl group which may be optionally substituted.

10. The compound of claim 4, where R² represents a silyl group which may be optionally substituted.

11. A method for reducing the accumulation of cholesterol in the artery wall comprising administering to a subject in need thereof an effective amount of the compound of claim 1.

12. The method of claim 11, wherein said subject has arteriosclerosis.

13. The method of claim 11, wherein said subject has hyper-lipidemia.

14. The method of claim 11, wherein said compound is parenterally administered to said subject.

* * * * *